(12) United States Patent
Bott et al.

(10) Patent No.: US 10,195,072 B2
(45) Date of Patent: Feb. 5, 2019

(54) DEVICES AND METHODS FOR COOLING PATIENTS

(71) Applicant: OHIO STATE INNOVATION FOUNDATION, Columbus, OH (US)

(72) Inventors: James Michael Bott, Columbus, OH (US); Jeremy Ryan Hughes, Granville, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 514 days.

(21) Appl. No.: 14/773,579

(22) PCT Filed: Mar. 11, 2014

(86) PCT No.: PCT/US2014/023501
§ 371 (c)(1),
(2) Date: Sep. 8, 2015

(87) PCT Pub. No.: WO2014/164795
PCT Pub. Date: Oct. 9, 2014

(65) Prior Publication Data
US 2016/0015558 A1 Jan. 21, 2016

Related U.S. Application Data

(60) Provisional application No. 61/775,856, filed on Mar. 11, 2013.

(51) Int. Cl.
*A61F 7/00* (2006.01)
*A61M 16/08* (2006.01)
(Continued)

(52) U.S. Cl.
CPC ........... *A61F 7/00* (2013.01); *A61M 16/0875* (2013.01); *A61F 2007/0064* (2013.01);
(Continued)

(58) Field of Classification Search
CPC .................................. A61F 2007/006; A61F 2007/0063–2007/0065; A61F 2007/0067; A61F 2007/0068
See application file for complete search history.

(56) References Cited

U.S. PATENT DOCUMENTS 3,336,921 A * 8/1967 Lloyd ................ A61H 33/0091
4/559
3,537,448 A 11/1970 Liston
(Continued)

OTHER PUBLICATIONS

Galbraith, S. et al., "Does the Use of a Handheld Fan Improve Chronic Dyspnea? A Randomized, Controlled, Crossover Trial," Journal of Pain and Symptom Management, 2010, vol. 39, No. 5, pp. 831-838.
(Continued)

*Primary Examiner* — Kaitlyn Smith
(74) *Attorney, Agent, or Firm* — Michael Best & Friedrich LLP

(57) ABSTRACT

A pneumatic cooling device including a housing having a first end and a second end. A handle extends from an outer surface of the housing. An inlet is positioned at substantially the first end of the housing and is configured to receive a supply of medical grade air into the housing. An outlet is positioned at substantially the second end of the housing and is configured to deliver the supply of medical grade air outside of the housing. A pathway extends through the housing between the inlet and the outlet and is configured to passively move the supply of medical grade air between the inlet and the outlet.

17 Claims, 9 Drawing Sheets

(51) Int. Cl.
*A61G 7/05* (2006.01)
*A61G 13/10* (2006.01)

(52) U.S. Cl.
CPC .............. *A61G 7/05* (2013.01); *A61G 13/101* (2013.01); *A61G 13/108* (2013.01); *A61G 2210/70* (2013.01); *A61M 2205/362* (2013.01); *A61M 2205/3606* (2013.01); *A61M 2209/082* (2013.01); *A61M 2209/088* (2013.01)

(56) References Cited

U.S. PATENT DOCUMENTS

| | | | |
|---|---|---|---|
| 3,675,275 A | 7/1972 | Arblaster | |
| 4,511,163 A | 4/1985 | Harris et al. | |
| 5,389,037 A | 2/1995 | Hale | |
| 7,001,416 B2* | 2/2006 | Augustine | A61F 7/00 607/104 |
| 7,543,583 B2* | 6/2009 | Acton | A47C 21/044 128/200.28 |
| 7,837,721 B2* | 11/2010 | Augustine | A61F 7/00 607/104 |
| 8,597,339 B2* | 12/2013 | Augustine | A61F 7/00 607/104 |
| 2003/0195596 A1* | 10/2003 | Augustine | A61F 7/00 607/104 |
| 2005/0143796 A1* | 6/2005 | Augustine | A61F 7/00 607/104 |
| 2006/0052853 A1* | 3/2006 | Augustine | A61F 7/00 607/104 |
| 2008/0195184 A1* | 8/2008 | Ziaimehr | A61F 7/0085 607/104 |
| 2009/0165799 A1* | 7/2009 | Duquette | A61M 16/0666 128/204.25 |
| 2011/0017213 A1* | 1/2011 | Vadney | A61M 16/0875 128/204.17 |
| 2011/0022135 A1* | 1/2011 | Augustine | A61F 7/00 607/104 |
| 2012/0053482 A1* | 3/2012 | Addington | A61M 11/02 600/538 |
| 2012/0190999 A1* | 7/2012 | Addington | A61M 11/02 600/538 |
| 2013/0047987 A1 | 2/2013 | Mays | |
| 2013/0174838 A1 | 7/2013 | Youngblood | |
| 2014/0058485 A1* | 2/2014 | Augustine | A61F 7/00 607/107 |
| 2014/0207016 A1* | 7/2014 | Addington | A61M 15/0036 600/538 |
| 2015/0126927 A1* | 5/2015 | Flickinger | A61M 11/06 604/147 |
| 2015/0239646 A1* | 8/2015 | Behar | B05B 11/0064 222/630 |

OTHER PUBLICATIONS

Shumway, N. M. et al., "Presence and treatment of air hunger in severely ill patients," Respiratory Medicine, 2008, 102, 27-31.
Kerr, D., "A bedside fan for terminal dyspnea," American Journal of Hospice and Palliative Medicine, 1989, 6: 22.
Schwartzstein, R. M. et al., "Cold Facial Stimulation Reduces Breathlessness Induced in Normal Subjects," Am Rev Respir Dis, 1987, 136: 58-61.
Freedman, S., "Facial Cooling and Perception of Dyspnoea," The Lancet, 1987, vol. 330, No. 8563, p. 836.
Thompson, H. J. et al., "Fever Management Practices of Neuroscience Nurses: National and Regional Perspectives," J Neurosci Nurs., 2007, 39(3): 151-162.
International Search Report and Written Opinion for Application No. PCT/US2014/023501 dated Jul. 10, 2014 (13 pages).

* cited by examiner

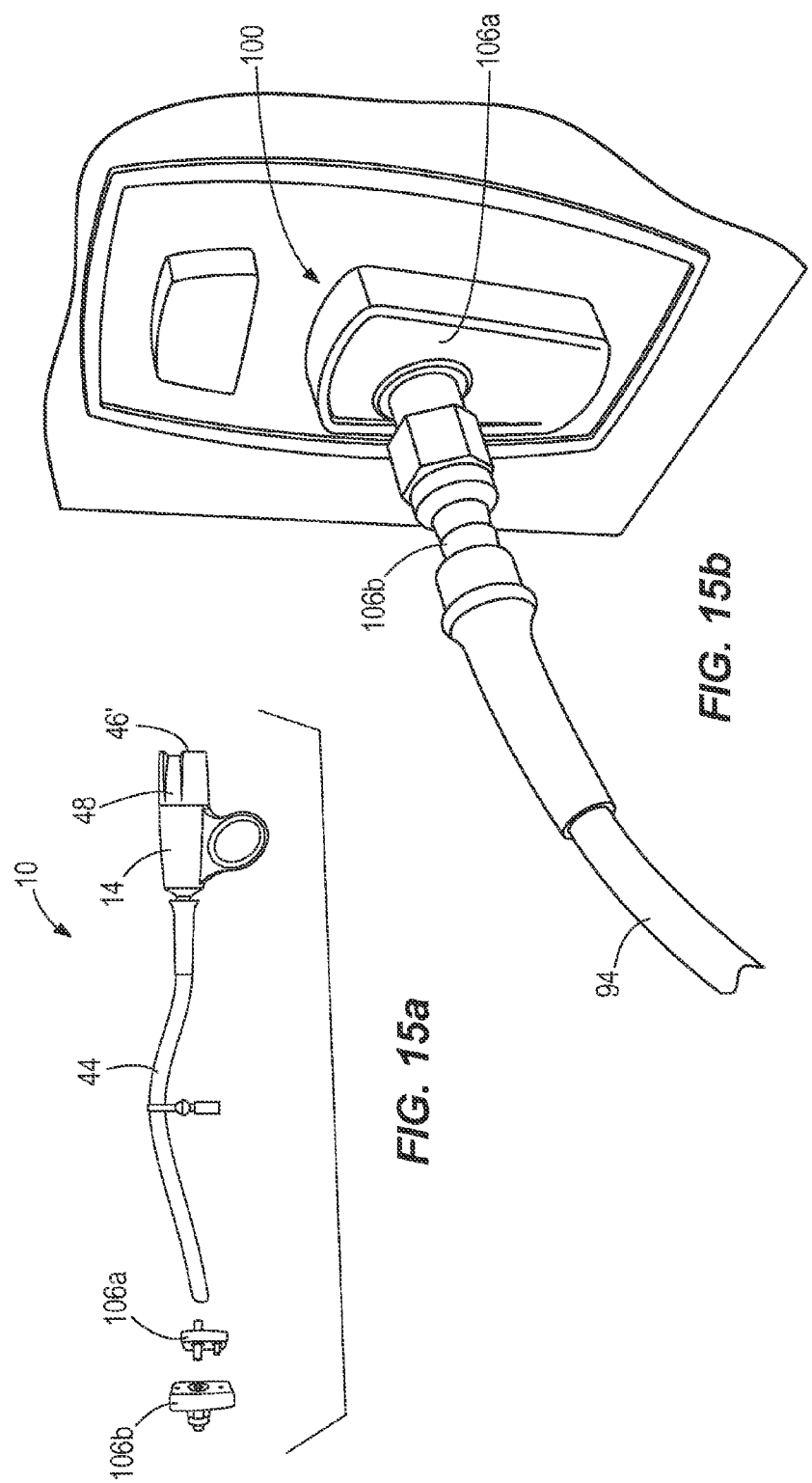

DEVICES AND METHODS FOR COOLING PATIENTS

CROSS-REFERENCE TO RELATED APPLICATIONS

This application is a national stage filing under 35 U.S.C. § 371 of International Application No. PCT/US2014/023501, filed Mar. 11, 2014, which claims priority to U.S. Provisional Application No. 61/775,856, filed Mar. 11, 2013, the entire contents of both applications are incorporated herein by reference.

BACKGROUND OF THE INVENTION

Air movement is critical for patients in a hospital to reduce the symptoms of anxiety (i.e., breathlessness, sweating, etc.). Air movement is therefore helpful in keeping patients cool and comfortable. Typically, fans are used to create air movement. It is common for hospitals to prohibit cooling fans because bacteria and other pathogens can reside on the blades of fans, which are then propelled into the air and may cause or spread illness and infection. Therefore, it is difficult to supply patients with cooled, moving air in the hospital setting.

SUMMARY OF THE INVENTION

The present invention relates to a pneumatic cooling device, and more specifically to a personal air flow device for hospital or home use.

In one embodiment, the invention provides a pneumatic cooling device including a housing having a first end and a second end. A handle extends from an outer surface of the housing. An inlet is positioned at substantially the first end of the housing and is configured to receive a supply of medical grade air into the housing. An outlet is positioned at substantially the second end of the housing and is configured to deliver the supply of medical grade air outside of the housing. A pathway extends through the housing between the inlet and the outlet and includes a first portion and a second portion. The first portion has a first diameter and the second portion has a second diameter less than the first diameter.

In another embodiment, the invention provides a pneumatic cooling device including a housing having a first end and a second end. A handle extends from an outer surface of the housing. An inlet is positioned at substantially the first end of the housing and is configured to receive a supply of medical grade air into the housing. An outlet is positioned at substantially the second end of the housing and is configured to deliver the supply of medical grade air outside of the housing.

In a further embodiment, the invention provides a pneumatic cooling device including a housing having a first end and a second end. A handle extends from an outer surface of the housing. A pathway extends through the housing between the inlet and the outlet and includes a first portion and a second portion. The first portion defines a first velocity of the supply of the medical grade air and the second portion defines a second velocity of the supply of the medical grade air. The second velocity is greater than the first velocity.

Other aspects of the invention will become apparent by consideration of the detailed description and accompanying drawings.

BRIEF DESCRIPTION OF THE DRAWINGS

FIG. 15a is a perspective view of a pneumatic cooling device including a standardized medical air connection and an adjustment mechanism.

FIG. 15b is a detailed perspective view of the standardized medical air connection of FIG. 15a.

DETAILED DESCRIPTION

Figure 1:
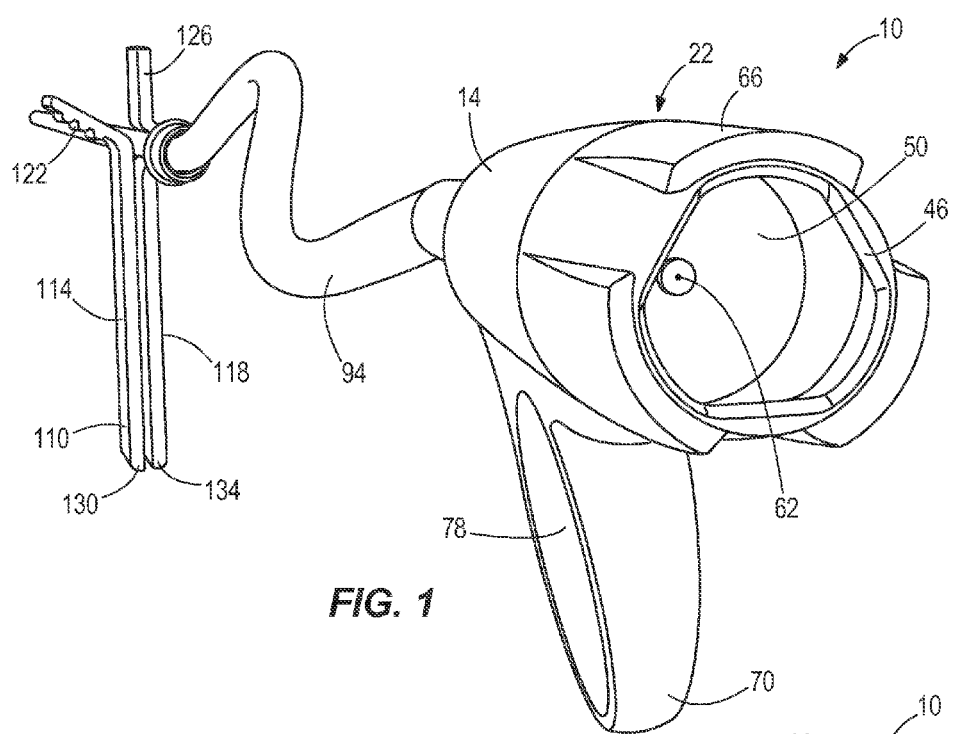
FIG. 1 is a front perspective view of a first side of a pneumatic cooling device according to an embodiment of the invention.
Figure 2:
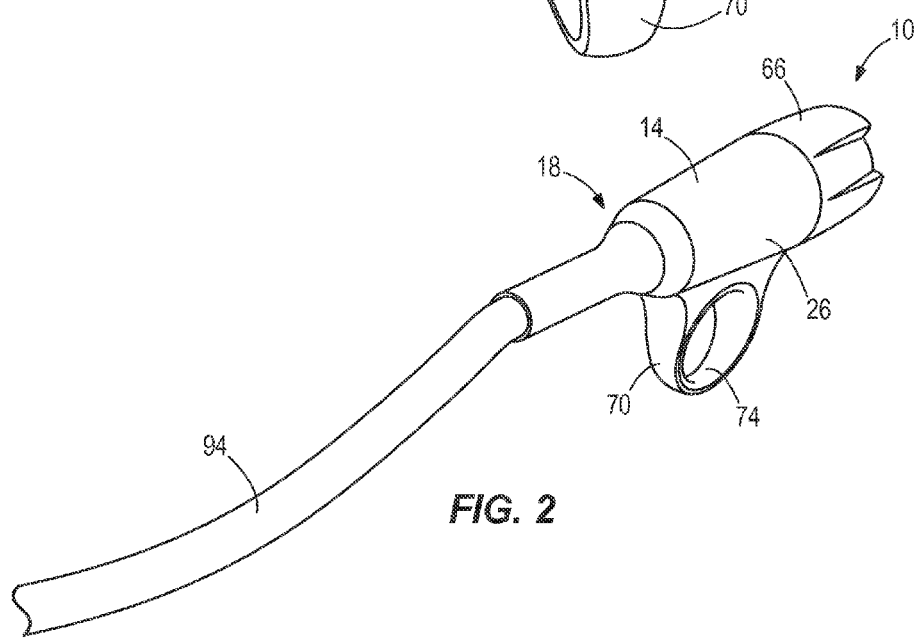
FIG. 2 is a rear perspective view of the pneumatic cooling device illustrated in FIG. 1.
Figure 3:
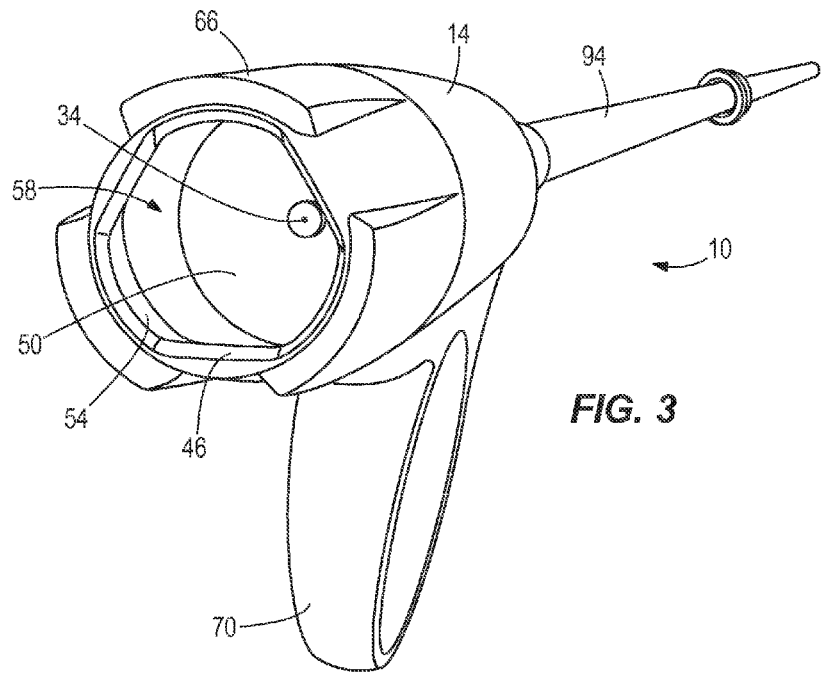
FIG. 3 is a front perspective view of a second side of the pneumatic cooling device illustrated in FIG. 1.
Figure 4:
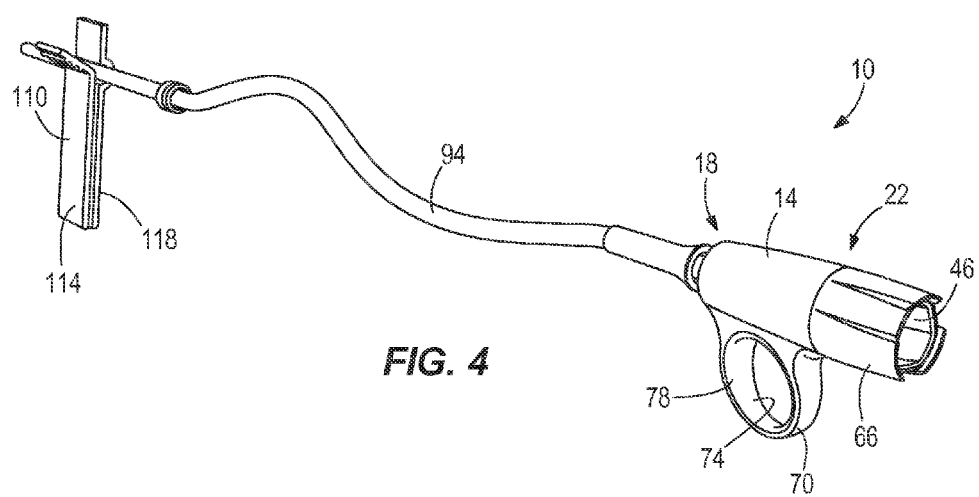
FIG. 4 is a perspective view of the first side of the pneumatic cooling device illustrated in FIG. 1.
Figure 5:
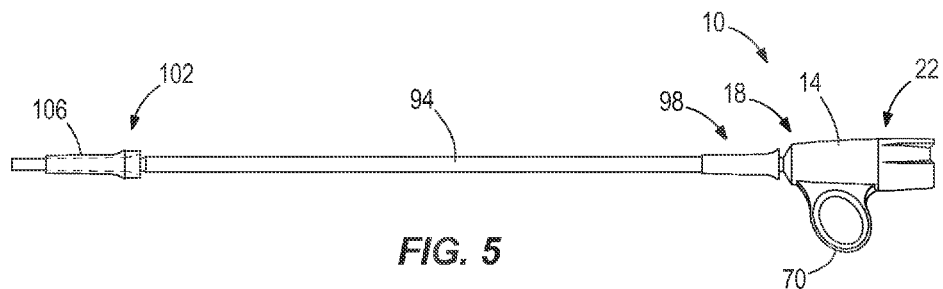
FIG. 5 is a side view of the pneumatic cooling device illustrated FIG. 1 connected to an air supply tube.
Figure 6:
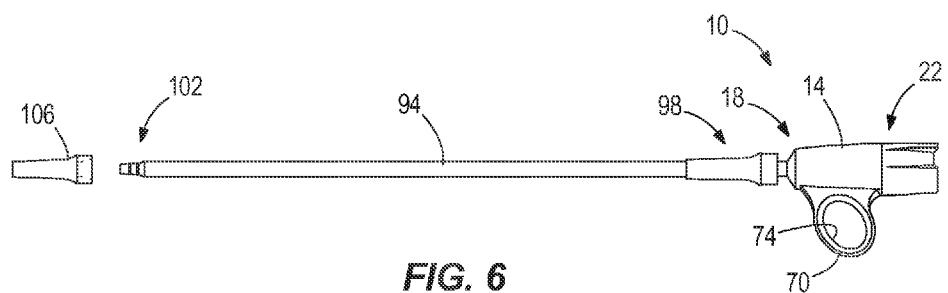
FIG. 6 is a side view of the pneumatic cooling device of FIG. 5 disconnected from the air supply tube.
Figure 7:
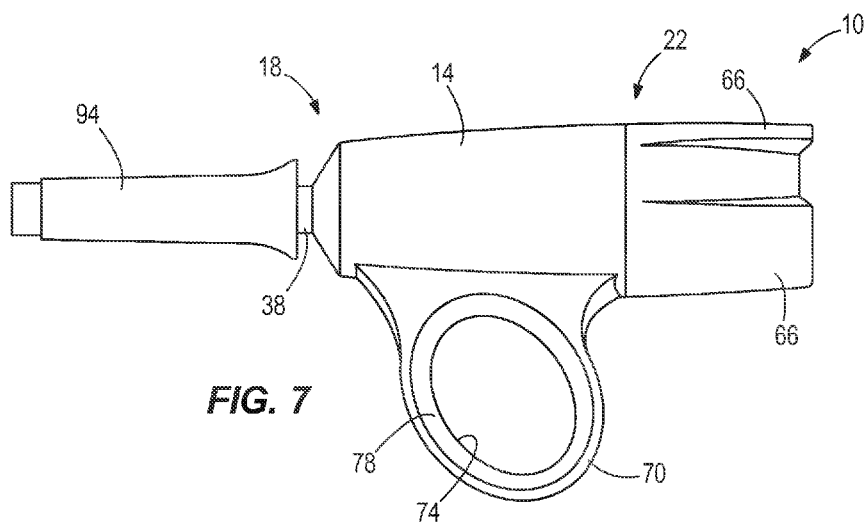
FIG. 7 is a detailed view of a portion of the pneumatic cooling device illustrated in FIG. 1.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The pneumatic cooling device described herein is a low cost alternative to more expensive means of cooling patients and utilizes filtered medical air which hospitals have in most patient rooms and is disposable, therefore negating any spread of infection from patient to patient. The present invention relates to a completely pneumatic, multi-directional, bladeless, personal cooling device that utilizes the venturi effect to increase low flow medical air into higher flow, providing patients with a means of cooling themselves.

FIGS. 1-8 illustrate a pneumatic cooling device 10 according to one embodiment of the invention. The device 10 includes a housing 14 having a first end 18 and a second end 22. A body 26 of the housing 14 is defined between the first end 18 and the second end 22. The housing 14 includes an inlet 30 that is positioned substantially at the first end 18 and an outlet 34 that is positioned substantially at the second end 22. In the illustrated embodiment, the housing 14 is constructed from plastic, although in alternative embodiments the housing may be constructed from other suitable materials (i.e., metal or other types of polymers, etc.)

In the illustrated embodiment, the device 10 includes a projection 38 (FIG. 8) formed as one piece with the first end of the housing 14. The projection 38 includes a stepped outer surface 42 in which the circumference of the projection increases from the distal end to the body 26. The projection 38 may have outer surfaces having alternative contours. The inlet 30 is positioned at a distal end of the projection 38. The projection 38, like the housing 14, is constructed from a plastic material but may be constructed from other suitable materials, as discussed above. Additionally, the projection 38 may be constructed separately and coupled to the housing (i.e., by an adhesive or threaded coupling, etc.).

Further, the second end 22 of device 10 includes a head 46 that is rotatably (e.g., threadingly) coupled to the body 26 of the device 10. The head 46 includes a surface 50 that defines a closed end of the housing 14 when coupled thereto. The head 46 also includes an open end 54 that is spaced apart from the closed end 50 thereby defining an opening 58 that extends from the second end 22 of the housing 14 to the open end 54 of the head 46. The surface 50 includes an aperture 62 that defines the outlet 34 of the device 10. The aperture 62 includes an adjustable flow valve, which will be discussed in greater detail below. As illustrated, the outlet 34 is recessed with respect to the open end 58 of the head 46 within the opening 58. In the illustrated embodiment, the closed end 50 of the head 46 is substantially circular and concentric with the second end 22 of the housing 14, while the open end 54 and the opening of the head 46 is substantially triangularly shaped. In other embodiments, the head may have different dimensions and shapes. The head is constructed from plastic, although in alternative embodiments the head may be constructed from other suitable materials, like the housing discussed above. Further, the illustrated head includes an auxiliary outer or gripping surface 66 that is constructed from silicone rubber, for example. In other embodiments, the gripping surface may be omitted or be constructed from alternative materials. Additionally, as illustrated in FIG. 15a, the head 46' may also be displaced at an angle with respect to the housing 14. The angular offset may be accomplished by an angular head or an angular attachment 48 that may be coupled between the housing 14 and the head 46'.

A handle 70 is formed as one piece with and extends from the housing 14. In the illustrated embodiment, the handle 14 is substantially circular and defines a substantially circular aperture 74. Further, the illustrated handle 70 extends from the body 26 of the device 10. In other embodiments, the handle 70 could be positioned in other locations and have other configurations, which will be discussed in greater detail below. The handle 70, like the housing, is constructed from a plastic material but may be constructed from other suitable materials, as discussed above. The illustrated handle 70 also includes a silicone rubber gripping surface 78 that is concentric with the aperture. The gripping surface 78 ensures patient comfort. The gripping surface 78 may be constructed from another suitable material. Additionally, the handle 70 may be constructed separately and coupled to the housing (i.e., by an adhesive coupling, etc.).

The device 10 includes a pathway 82 (FIG. 8) that extends through the housing 14 between the inlet 30 and the outlet 34. In the illustrated embodiments, the pathway 82 extends from the inlet 30 at the distal end of the projection 38, through the projection 38, to the aperture 62 in the head 46 at the second end 22 of the housing 44. The inlet 30 is configured to receive air or other gases that is guided through the housing 14 by the pathway 82 to the outlet 22, which is configured to deliver the air outside of the housing 14 and beyond the open end 54 of the head 46. The device 10 may be used with medical grade air, which is typically associated with breathing devices such as mechanical ventilators, oxygen masks, medical nebulizers, and non-invasive devices including continuous positive airway pressure (CPAP) and bilateral positive airway pressure (BiPAP) devices.

Figure 8:
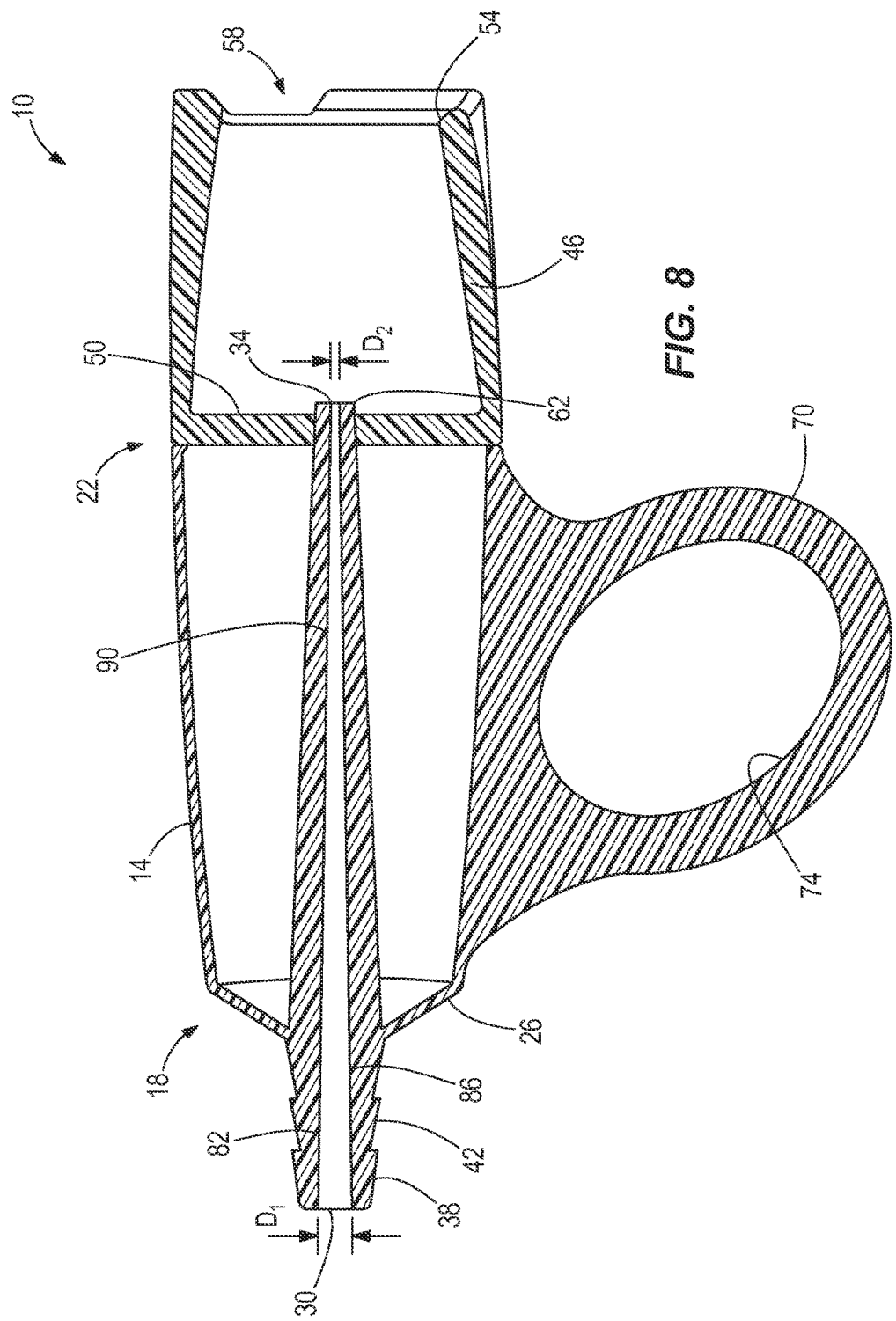
FIG. 8 is a cross-sectional view of the pneumatic cooling device illustrated in FIG. 1.

Further with continued reference to FIG. 8, the pathway 82 in the housing 14 includes a first portion 86 and a second portion 90. The first portion 86 extends from the inlet 30 at least partially through the housing 14. In the illustrated embodiment, the first portion 86 of the pathway 82 extends at least partially through the projection 38 as well. The first portion 86 of the pathway 82 defines a first diameter $D_1$. The second portion 90 extends from the first portion to the outlet 34 and is defined by a second diameter $D_2$. The first diameter $D_1$ tapers gradually to the second diameter $D_2$ such that the second diameter $D_2$ is smaller than the first diameter $D_1$ thereby creating a venturi effect. In other words, the narrowing of the pathway 82 (i.e., decrease in cross-sectional area) between the first portion 86 and the second portion 90 increases the velocity of the air passing therethrough. As such, the first portion 86 defines a first velocity of the air in the pathway and the second portion 90 defines a second velocity of the air passing through the pathway. The second velocity is greater than the first velocity as defined by the venturi effect. As a result, the housing 14 is able to passively guide the air along the pathway 82 between the inlet 30 and the outlet 34 of the housing 14. In other words, the device 10 does not include rotating blades or an active feature that is responsible for moving the air through the housing 14 and expelling the air from the housing 14. In the illustrated embodiment, the second portion 90 terminates at the aperture 62 in the head 46, which includes the adjustable control valve. Rotation of the head 46 relative to the housing 14 determines the position of the valve in order to control or determine the flow rate of the air expelled from the aperture 62. The taper between the first portion 86 and the second portion 90 advantageously prevents a whistling effect created by a sudden change in diameter between the two portions.

Further with respect to FIGS. 1-7, air is guided to the inlet 30 by a hose or tube 94 that is removably coupled between the first end 18 of the housing 14 and an air supply 100 (FIG. 15b). As illustrated, the hose 94 is removably secured to the inlet 30, and specifically the projection 38 of the device 10. In particular, the hose 94 defines a conduit having an inner diameter and first end 98 that receives and grips the stepped outer surface 42 of the projection 38. The conduit includes a 0.25 inch inner diameter but may be larger or smaller depending on the hose 94. A second end 102 of the hose 94 is removably secured to a standard air connection 106a, which can then be coupled to a standard air connection 106b (FIGS. 15a and 15b) of any air supply source (i.e., a compressed air tank, an air pump, or the like). The hose 94 is constructed from silicone rubber, for example, or any other suitable flexible material that allows the hose 94 to bend without kinking. As such, the device 10 is easily manipulated or movable relative to the air supply source depending on the needs of the patient. Also, because the hose 94 does not kink, bacteria and germs are less likely to build-up within the conduit and airflow therethrough is less likely to be impeded. While the hose 94 of FIGS. 1-8 has a smooth contour, it may include any suitable contour such as a ribbed outer surface.

Figure 12:
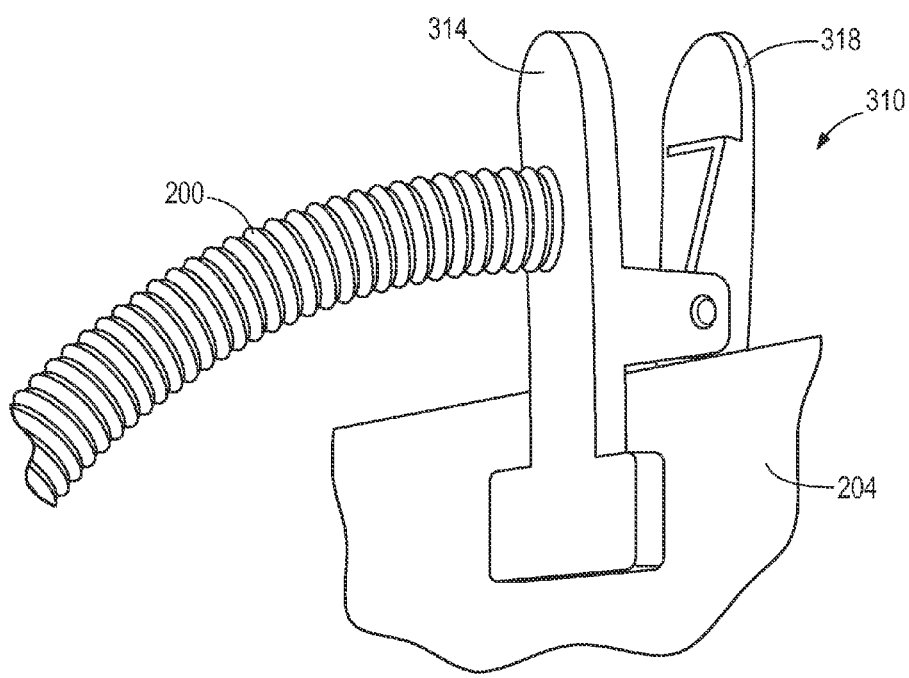
FIGS. 12-14 are perspective view of clips having alternative configurations that may be used in conjunction with the pneumatic cooling device illustrated in FIG. 1.
Figure 13B:
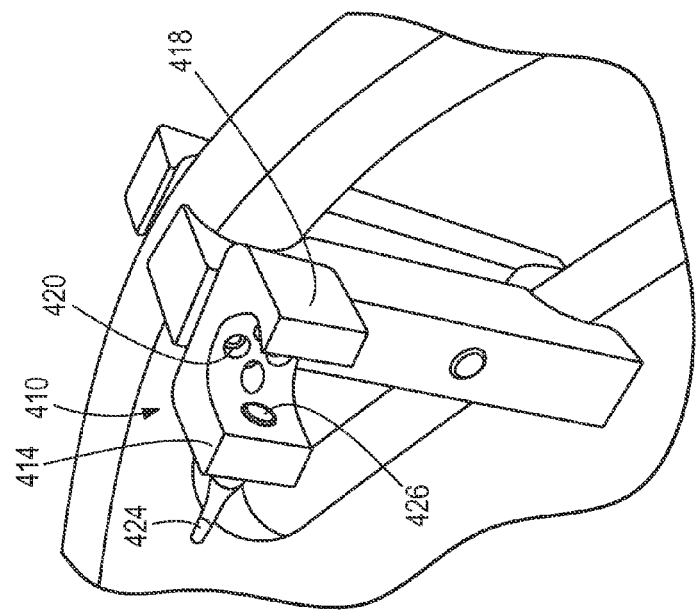
Figure 13A:
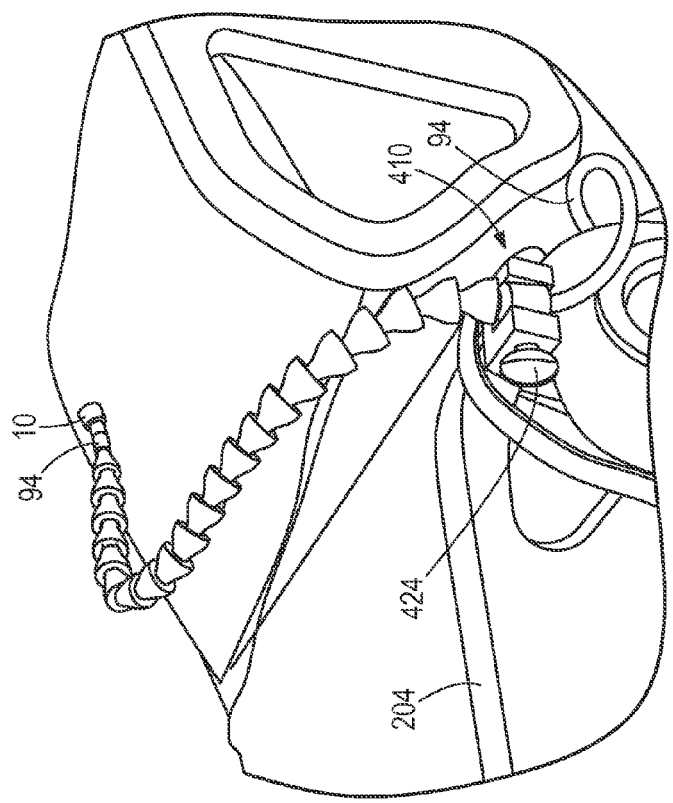

In alternative embodiments, the hose 94 may extend through an outer, more rigid structure 200. For example, FIGS. 12 and 13a illustrate a larger, stiffer conduit 200 that may receive the hose 94. As such, the hose 94, while still easily manipulatable relative to the user, may be suspended above a hospital bed or chair 204, for example.

Further with respect to FIGS. 1-7, a clip 110 may be removably secured to and slidable along the hose 94. The illustrated clip 110 includes a first leg 114 that is pivotably coupled to a second leg 118. The hose 94 extends between the two legs 114, 118. A handle portion 122, 126 of each of the first and the second legs 114, 118 may be moved toward and away from one another to move distal ends 130, 134 of each of the first and the second legs 114, 118 away from and toward one another, respectively. As such the distal end 130, 134 of the first and the second legs 114, 118 may be clamped to a support such as a bed sheet or an article of clothing. The clip 110 anchors the hose 94 relative to the patient and prevents the hose 94 from becoming disengaged from either the air supply source or the device 10.

Figure 14:
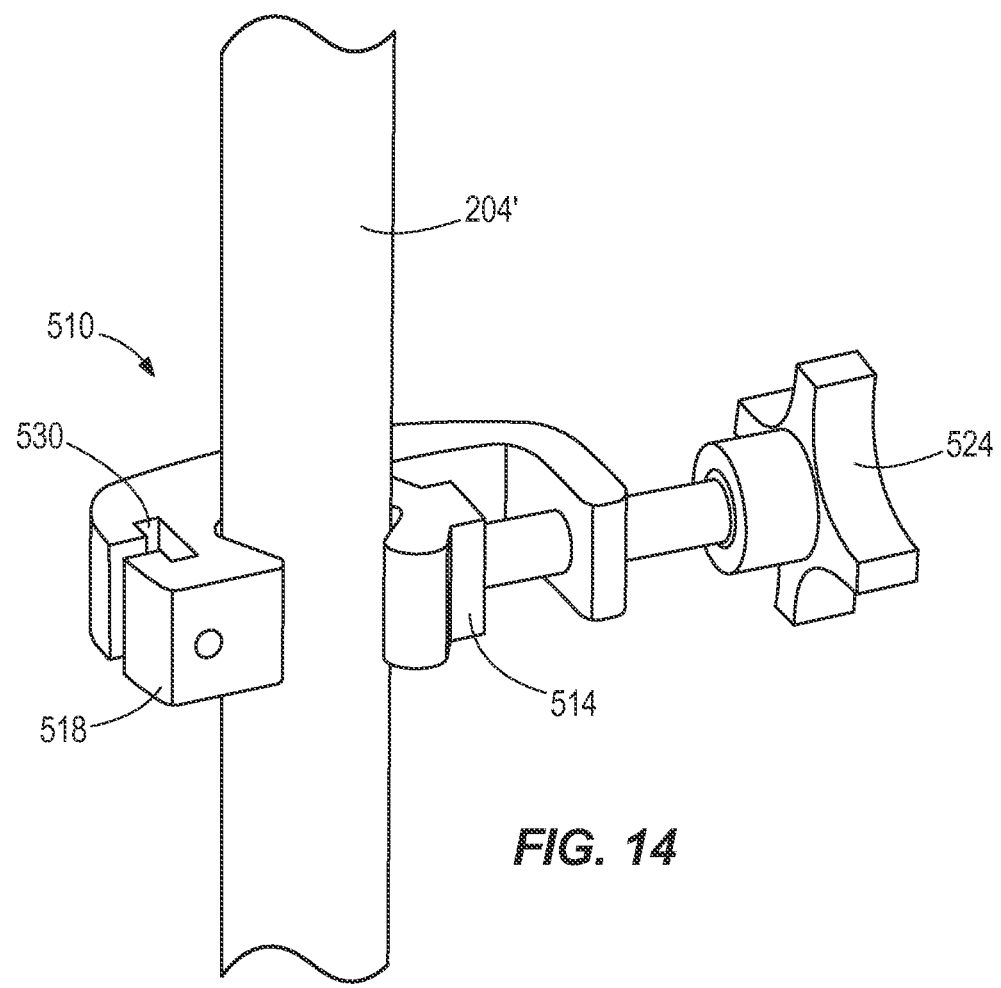

The clip 110 may have alternative configurations. For example, a clip 310 may be coupled to either the hose 94 or the rigid conduit 200. The clip 310 also couples to a hospital bed 204. As illustrated in FIG. 12, the legs 314, 318 are pivotable relative to one another to grip opposite sides of a rail of the bed 204. FIGS. 13a and 13b illustrate another embodiment of a clip 410. Clip 410 includes two legs 414, 418 spaced apart from one another defining a channel 420 therebetween. A clamping member 424 is threadingly received in an aperture 426 of leg 514 such that a distal end of the clamping member 424 extends into the channel 420. The clamping member 424 couples the hose 94 or a rigid conduit 200 in the channel 420 between the leg 418 and the clamping member 424. As illustrated in FIG. 14, a channel 520 of clip 510 according to another embodiment of the invention may also be configured to receive and secure an IV stand 204'. The clip 520 also includes a recess 530 that is configured to receive the hose 94 therethrough.

Figure 9:
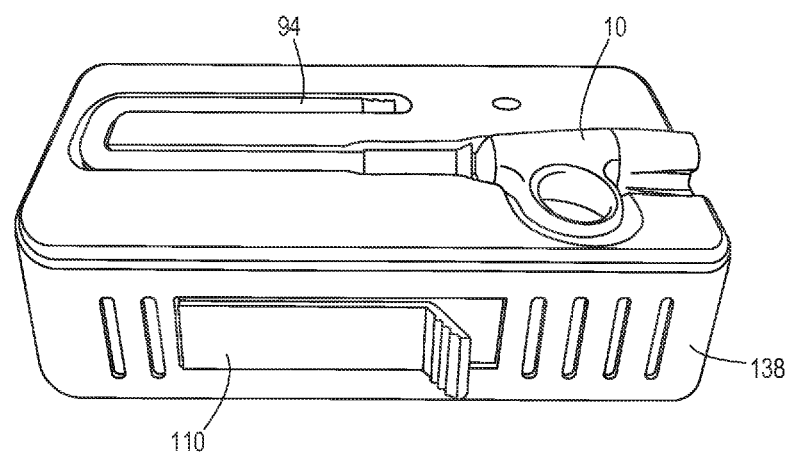
FIGS. 9-11 are perspective views of a kit including the pneumatic cooling device illustrated in FIG. 1.
Figure 10:
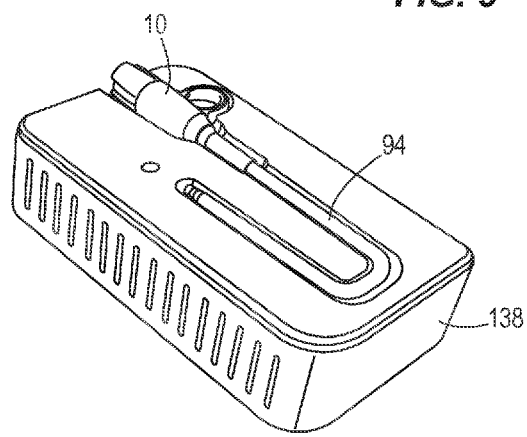
Figure 11:
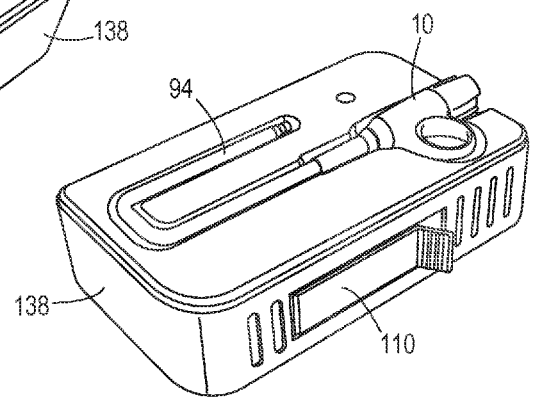

With respect to FIGS. 9-11, the device 10, the hose 94, and the clip 110 may be secured to a base 138. As such, the base 138, with the device 10, the hose 94, and the clip 110 secured thereto, is easily transportable.

The device 10 includes many advantages. For example, the device 10 may be disposable or sterilizable thereby negating the spread of infection from patient to patient. The venturi effect created by the pathway 82 extending through the housing also includes low airflow and therefore, low medical air consumption. The device 10 is pneumatic and uses the medical air outlet already located at a patient's bedside. The device 10 requires no electrical needs. Because the device 10 provides cool air passively (i.e., without blades, etc.), there is not dirt or dust accumulation. The device 10 is therefore safe for patients and visitors. The device 10 is also easily portable. Additionally the design of the device 10 differentiates the pneumatic cooling device from a medical device.

Various features and advantages of the invention are set forth in the following claims.

What is claimed is:

1. A portable pneumatic cooling device comprising:
a handheld housing including a first end and a second end;
a handle extending from an outer surface of the housing;
an inlet positioned at substantially the first end of the housing, the inlet configured to receive a supply of medical grade air into the housing,
an outlet positioned at substantially the second end of the housing, the outlet configured to deliver the supply of medical grade air outside of the housing, and
a pathway extending through the housing between the inlet and the outlet, the pathway having a first portion and a second portion, the first portion having a first diameter and the second portion having a second diameter less than the first diameter, wherein the pathway is configured to passively move the supply of medical grade air between the inlet and the outlet.

2. The pneumatic cooling device of claim 1 further comprising a flexible hose connecting the supply of medical grade air with the housing.

3. The pneumatic cooling device of claim 2 further comprising a clip configured to slide along the hose and to couple the hose to a support.

4. The pneumatic cooling device of claim 1, wherein the housing includes a projection formed as one piece with the housing and extending from the first end of the housing, the projection defining the inlet.

5. The pneumatic cooling device of claim 4, wherein the projection at least partially defines the first portion of the pathway.

6. The pneumatic cooling device of claim 4, wherein the projection includes a stepped outer surface in which a circumference of the projection increases from a distal end to the housing.

7. The pneumatic cooling device of claim 4, wherein the projection is configured to removably secure a first end of a flexible hose, the flexible hose including a second, opposite end configured to couple to the supply of medical grade air.

8. The pneumatic cooling device of claim 1, further comprising a gripping head coupled to and extending from the second end of the housing beyond the outlet, the gripping head surrounding the outlet.

9. A portable pneumatic cooling device comprising:
a handheld housing including a first end and a second end;
a handle extending from an outer surface of the housing;
an inlet positioned at substantially the first end of the housing, the inlet configured to receive a supply of medical grade air into the housing,
an outlet positioned at substantially the second end of the housing, the outlet configured to deliver the supply of medical grade air outside of the housing, and
a pathway extending through the housing between the inlet and the outlet, the pathway having a first portion and a second portion, the first portion defining a first velocity of the supply of the medical grade air and the second portion defining a second velocity of the supply of the medical grade air, the second velocity being greater than the first velocity, wherein the pathway is configured to passively move the supply of medical grade air between the inlet and the outlet.

10. The pneumatic cooling device of claim 9, wherein the first portion defines a first diameter and the second portion defines a second diameter less than the first diameter.

11. The pneumatic cooling device of claim 9 further comprising a flexible hose connecting the supply of medical grade air with the housing.

12. The pneumatic cooling device of claim 11 further comprising a clip configured to slide along the hose and to couple the hose to a support.

13. A portable pneumatic cooling device comprising:
a handheld housing including a first end and a second end;
a handle extending from an outer surface of the housing;
an inlet positioned at substantially the first end of the housing, the inlet configured to receive a supply of medical grade air into the housing,
an outlet positioned at substantially the second end of the housing, the outlet configured to deliver the supply of medical grade air outside of the housing, and
a pathway extending through the housing between the inlet and the outlet, the pathway configured to passively move the supply of medical grade air between the inlet and the outlet, the pathway having a first portion and a second portion, wherein the pathway is tapered between the first portion and the second portion such that a diameter of the pathway gradually narrows from the first portion to the second portion.

14. The pneumatic cooling device of claim 13, wherein the first portion includes a first diameter and the second portion includes a second diameter less than the first diameter.

15. The pneumatic cooling device of claim 14, wherein the first portion defines a first velocity of the supply of the medical grade air and the second portion defines a second velocity of the supply of the medical grade air, the second velocity being greater than the first velocity.

16. The pneumatic cooling device of claim 13 further comprising a flexible hose connecting the supply of medical grade air with the housing.

17. The pneumatic cooling device of claim 16 further comprising a clip configured to slide along the hose and to couple the hose to a support.

* * * * *